United States Patent
Stratis et al.

(10) Patent No.: US 9,972,907 B2
(45) Date of Patent: May 15, 2018

(54) METHOD FOR PLASMA DYNAMIC CANCELLATION FOR HYPERSONIC VEHICLES

(71) Applicant: Raytheon Company, Waltham, MA (US)

(72) Inventors: Glafkos K. Stratis, Lake Worth, FL (US); Anton Vanderwyst, Tucson, AZ (US); Wayne L. Sunne, Tucson, AZ (US); David G. Derrick, Vail, AZ (US); James P. Edmiston, Allen, TX (US); David G. Manzi, Tucson, AZ (US); Howard C. Choe, Southlake, TX (US); Alphonso A. Samuel, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 116 days.

(21) Appl. No.: 15/068,026

(22) Filed: Mar. 11, 2016

(65) Prior Publication Data

US 2017/0264015 A1    Sep. 14, 2017

(51) Int. Cl.
*H01Q 3/34* (2006.01)
*G01N 9/24* (2006.01)
(Continued)

(52) U.S. Cl.
CPC ............ *H01Q 3/34* (2013.01); *B64C 30/00* (2013.01); *B64G 1/66* (2013.01); *F42B 15/10* (2013.01);
(Continued)

(58) Field of Classification Search
CPC ............ H01Q 3/34; H01Q 1/42; H01Q 21/20
(Continued)

(56) References Cited

U.S. PATENT DOCUMENTS 3,176,227 A * 3/1965 Bender ............... F03H 1/00
                                                    244/3.21
3,296,531 A    1/1967 Seaton
(Continued)

FOREIGN PATENT DOCUMENTS

CN          105329465 A       2/2016

OTHER PUBLICATIONS

James P. Rybak et al; "Progress in Reentry Communications", IEEE Transactions on Aerospace and Electronic Systems, IEEE Service Center, Piscataway, NJ, US, vol. AES-10, No. 5, Sep. 1, 1971 (Sep. 1, 1971), pp. 879-894, XP011167819, ISSN: 0018-9251.
(Continued)

*Primary Examiner* — Andrea Lindgren Baltzell
(74) *Attorney, Agent, or Firm* — Renner, Otto, Boisselle & Sklar, LLP (57) ABSTRACT

A sensor system and method of reducing plasma-induced communication inhibition for a main antenna includes using auxiliary antennas for detecting a density of plasma that affects operation of the main antenna, and re-orienting an electromagnetic field around the main antenna in response to the density detected to reduce effect of the plasma on the main antenna. The auxiliary antennas are also operable for data link communication and switchable such if the density of the plasma inhibits receipt or sending of signals by one of the auxiliary antennas, another one of the auxiliary antennas may be used for data link communication.

19 Claims, 4 Drawing Sheets

(51) Int. Cl.
*G01B 7/06* (2006.01)
*H01Q 21/20* (2006.01)
*H01Q 1/42* (2006.01)
*B64C 30/00* (2006.01)
*B64G 1/66* (2006.01)
*F42B 15/12* (2006.01)
*H01Q 1/28* (2006.01)
*H01Q 21/28* (2006.01)
*H05H 1/00* (2006.01)
*F42B 15/10* (2006.01)
*F42B 15/34* (2006.01)

(52) U.S. Cl.
CPC .............. *F42B 15/12* (2013.01); *F42B 15/34* (2013.01); *G01B 7/06* (2013.01); *G01N 9/24* (2013.01); *H01Q 1/281* (2013.01); *H01Q 1/42* (2013.01); *H01Q 21/20* (2013.01); *H01Q 21/28* (2013.01); *H05H 1/00* (2013.01); *H05H 1/0062* (2013.01)

(58) Field of Classification Search
USPC ......................................................... 343/705
See application file for complete search history.

(56) References Cited

U.S. PATENT DOCUMENTS 3,317,826 A    5/1967  Knop et al.
3,473,116 A   10/1969  Grantham
3,758,862 A *  9/1973  Tevelow .................. H04B 7/00
                                                    455/64
3,766,562 A   10/1973  Pollin

OTHER PUBLICATIONS

Priyanka Garg et al; "Reducing RF blackout during re-entry of the reuseable launch vehicle", Aerospace Conference, 2009 IEEE, IEEE, Piscataway, NJ, USA, Mar. 7, 2009 (Mar. 7, 2009), pp. 1-15, XP031449974, ISBN: 978-1-4244-2621-8.
International Search Report and Written Opinion for corresponding Application No. PCT/US2016/057860 dated Jan. 30, 2017.
Ganiev et al., "Aerodynamic Drag Reduction by Plasma and Hot-Gas Injection", Journal of Thermorphysics and Heat Transfer, vol. 14, No. 1, Jan.-Mar. 2000, pp. 10-17.
Davis et al., "Hypersonic or Re-Entry Plasma Communication", 17th AIAA International Space Planes and Hypersonic Systems and Technologies Conference, Apr. 11-14, 2011, San Francisco, California, AIAA 2011-2353, pp. 1-13.

* cited by examiner

METHOD FOR PLASMA DYNAMIC CANCELLATION FOR HYPERSONIC VEHICLES

FIELD OF THE INVENTION

The invention relates to a system and method for reducing plasma induced communication inhibition.

DESCRIPTION OF THE RELATED ART

When a vehicle travels at a hypersonic velocity, the kinetic energy of air molecules striking the surface of the vehicle generates a thermal and inertial shockwave in front of the vehicle. The collision of particles and the collision of particles with the surface of the vehicle creates heat, which effectively increases the air temperature, causing ionization of the particles or plasma formation which conforms with a flow field that is dependent on the shape of the hypersonic vehicle. For example, the flow field may include formation of a plasma of a blunt, or a tipped type of hypersonic platform. Alternatively the flow field may be around a sharp-tipped hypersonic vehicle. A dense plasma sheath is formed around the surface of the vehicle and may have a thickness of up to 30 centimeters, due to the ionization of particles by heating and particle collisions. The plasma layer impacts the operation of the vehicle by preventing normal communication of devices, or other wireless operations or radar functions within the vehicle. For example, plasma formation can disrupt radio signals emitted or received by the vehicle to communicate with a grounded control station, or a sensor used in target detection.

SUMMARY OF THE INVENTION

Plasma formation as previously described is highly dynamic and inhomogeneous around the surface of a hypersonic vehicle. The present application provides for adaptive capabilities in addressing the variations of plasma, including using diversity schemes among various antennas within the vehicle or dynamically changing electromagnetic fields according to the plasma behavior. A sensor system and method for reducing plasma-induced communication inhibition for a main antenna may be used in a hypersonic vehicle. The system includes a main antenna and at least one or more auxiliary antennas that are used for multiple functions within the vehicle including plasma sensing around the vehicle, reducing plasma in areas that inhibit the sending and/or receipt of signals by the main antenna, and providing data link communications for the vehicle.

According to an aspect of the invention, a sensor system includes: a main antenna; at least one auxiliary antenna; and a controller operatively coupled to the at least one auxiliary antenna. The controller receives information from the at least one auxiliary antenna regarding a plasma field that inhibits sending and receipt of signals by the main antenna. The controller also configures an electromagnetic field set up by the at least one auxiliary antenna to reduce density of the plasma field, to reduce, at least in part, inhibition by the plasma field of the sending and/or receipt of signals by the main antenna.

According to an aspect of the invention, the at least one auxiliary antenna may include a plurality of auxiliary antennas that are operable for data link communication.

According to an aspect of the invention, the plurality of auxiliary antennas may be switchable in response to density of the plasma field that inhibits the data link communication of one of the plurality of auxiliary antennas.

According to an aspect of the invention, the system may include at least one electromagnet for re-orienting the electromagnetic field.

According to an aspect of the invention, the at least one electromagnet may include a positively charged electromagnet and a negatively charged electromagnet that are spaced apart, and one of the positively charged electromagnet and the negatively charged electromagnet may be located distally opposite the main antenna.

According to an aspect of the invention, the system may include a positively or negatively charged two-phase electromagnet that is operable to change phase relative to an oppositely charged electromagnet.

According to an aspect of the invention, the system may include a plurality of electromagnets that are circumferentially spaced around the main antenna.

According to an aspect of the invention, system may include a plurality of auxiliary antennas that are circumferentially spaced around the main antenna. The plurality of auxiliary antennas may be diametrically opposed to one another.

According to an aspect of the invention, the system may be contained in a radome of a hypersonic vehicle.

According to an aspect of the invention, the radome may include a metallic tip that is negatively or positively charged, and a plurality of charged plates having an opposite charge from the metallic tip that are circumferentially spaced around the main antenna, wherein the metallic tip is located distally opposite the plurality of charged plates.

According to an aspect of the invention, an electromagnet may be coupled to the metallic tip for re-orienting the electromagnetic field.

According to an aspect of the invention, the at least one auxiliary antenna may have an ultra-wideband antenna structure.

According to an aspect of the invention, the at least one auxiliary antenna may have an omni-directional radiation pattern or a forward radiation pattern.

According to an aspect of the invention, a method of reducing plasma-induced communication inhibition for a main antenna includes: detecting a density of plasma that affects operation of the main antenna, and re-orienting an electromagnetic field around the main antenna in response to the density detected to reduce effect of the plasma on the main antenna.

According to an aspect of the invention, the method may further include using at least one auxiliary antenna to detect the density of the plasma and send information regarding the density of the plasma to a controller that is configured to re-orient the electromagnetic field.

According to an aspect of the invention, the method may further include using the at least one auxiliary antenna to generate the electromagnetic field.

According to an aspect of the invention, the method may further include using the at least one auxiliary antenna for data link communication.

According to an aspect of the invention, the method may further include switching between a first and second auxiliary antenna for data link communication in response to the density detected in a respective region of the first and second auxiliary antenna.

According to an aspect of the invention, the method may include using at least one electromagnet to re-orient the electromagnetic field.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

The annexed drawings, which are not necessarily to scale, show various aspects of the invention.

DETAILED DESCRIPTION

A sensor system and method for reducing plasma-induced communication inhibition for a main antenna may be used in a hypersonic vehicle. The system includes a main antenna and at least one auxiliary antenna that is used for multiple functions within the vehicle including plasma sensing around the vehicle, reducing plasma in areas that inhibit the sending and/or receipt of signals by the main antenna, and providing data link communications for the vehicle. The at least one antenna may include a plurality of antennas that are operable for switchable communication such that if plasma is detected to be inhibiting the communication of one of the antennas, another antenna may be used for communication. The use of at least one auxiliary antenna for multiple functions enables the system to accommodate for the dynamics of plasma while existing in a compact space of the vehicle. Furthermore, the sensor system may include a number of charged plates and/or electromagnets that, when combined with the auxiliary antennas, accommodate for the plasma by re-orienting the electromagnetic field or changing electric potentials in the system in response to the density of plasma.

Figure 1:
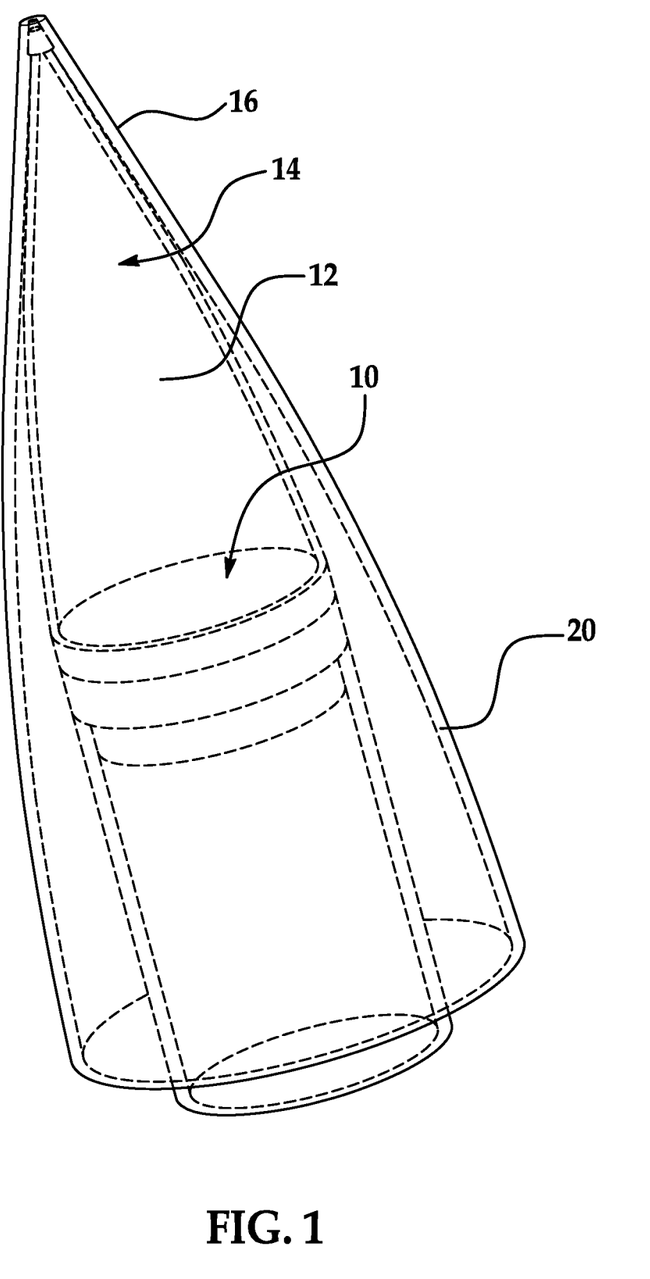
FIG. 1 is an oblique view of a hypersonic vehicle in accordance with the present invention.

Referring now to FIG. 1, a sensor system 10 may be contained in a radio frequency radome 12 located at the nose end 14 of a vehicle 16. The vehicle 16 may be a hypersonic vehicle, such as a high speed aircraft, missile, or spacecraft. A suitable missile may be a ballistic missile. The radome 12 is configured to cover the sensor system 10 and protect the system 10 from environmental conditions and mechanical stresses. The radome 12 may be conically-shaped and formed of any suitable material for withstanding aerodynamic heating and mechanical stresses. Examples of suitable materials include polymeric matrix composites, ceramic matrix composites, and monolithic ceramic materials. The radome 12 may also be substantially transparent to allow radio frequency radiation over broadband or narrowband frequencies.

Figure 2:
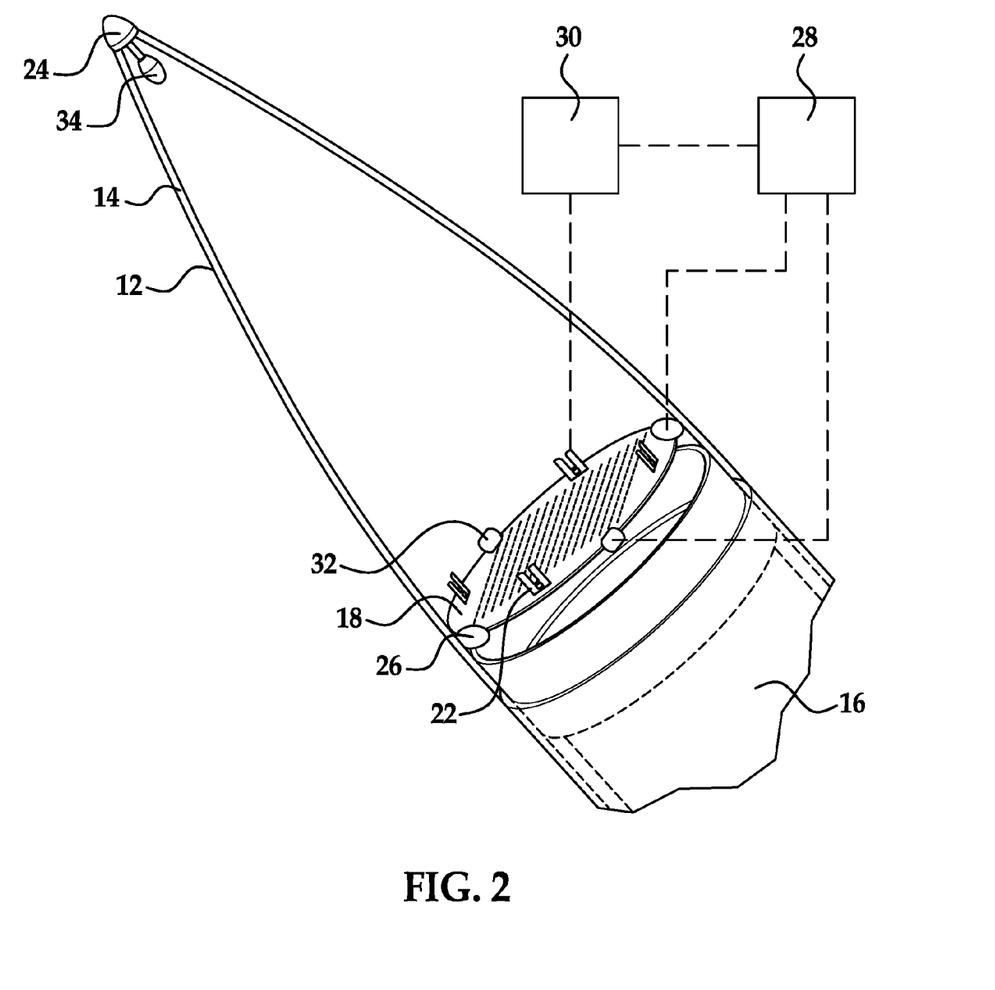
FIG. 2 is an oblique view of a radome in the hypersonic vehicle of FIG. 1 showing a sensor system in accordance with the present invention.
Figure 3A:
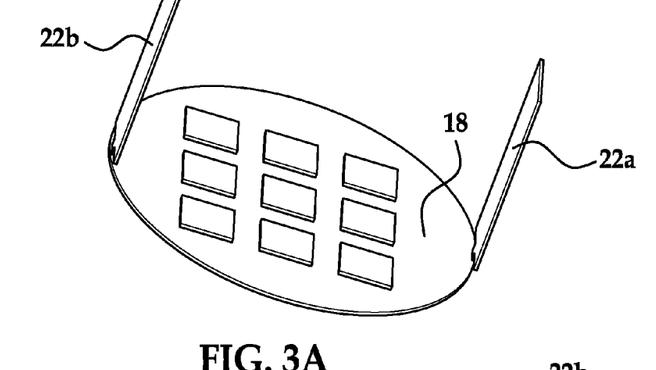
FIG. 3A is an oblique view of the sensor system of FIG. 2 showing a main antenna and dual auxiliary antennas in accordance with the present invention.
Figure 3B:
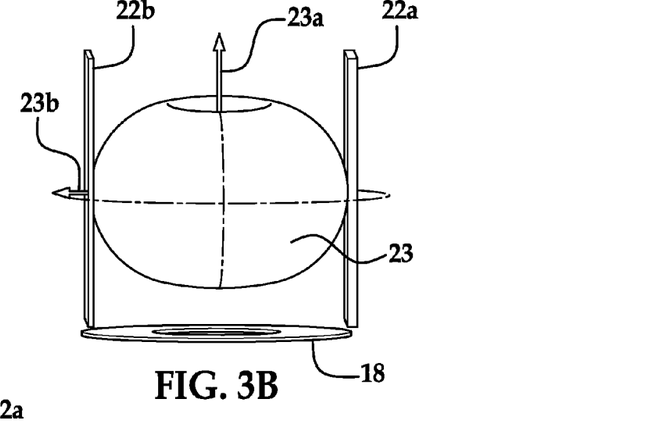
FIG. 3B is an oblique view of the dual auxiliary antennas of FIG. 3A showing the manipulation of plasma between the auxiliary antennas.
Figure 3C:
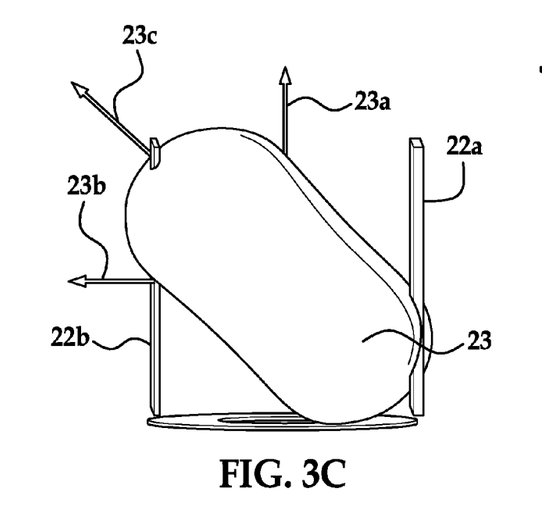
FIG. 3C is an oblique view of the dual auxiliary antennas of FIG. 3A showing another manipulation of the plasma.
Figures 3D, 4:
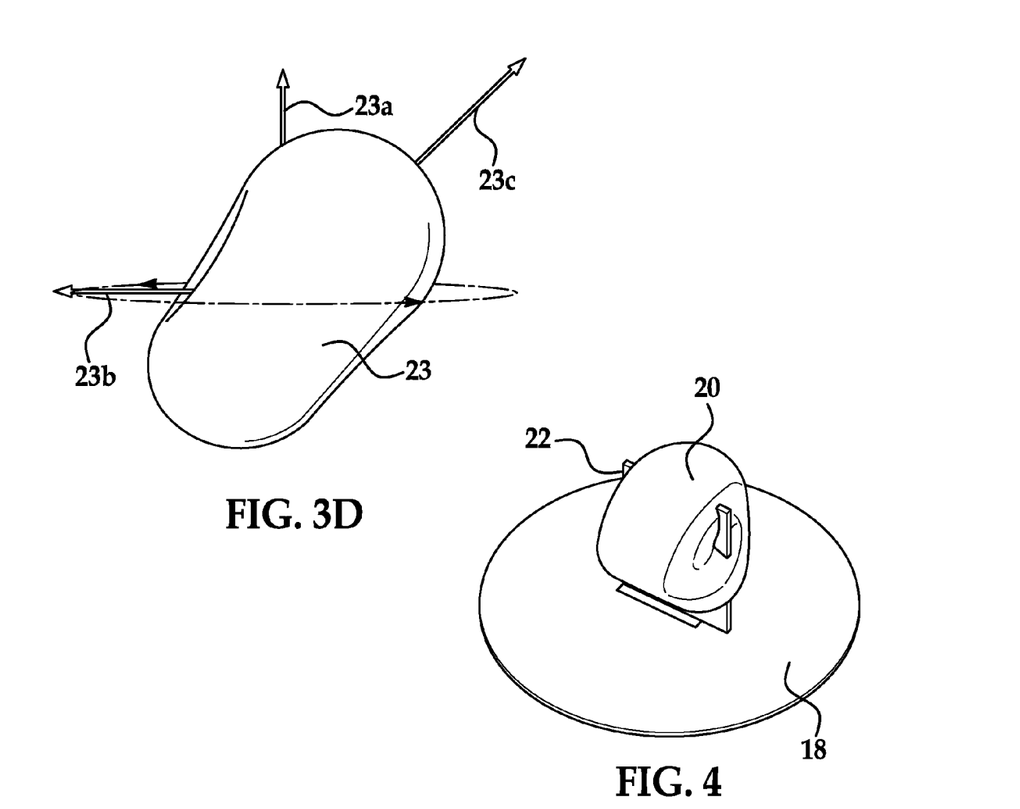
FIG. 3D is an oblique view of the manipulated plasma of FIG. 3C.
FIG. 4 is an oblique view of the auxiliary antenna of FIG. 3 in accordance with a first exemplary embodiment of the present invention.

Referring in addition to FIGS. 2-3D, the sensor system 10 may include a main antenna 18 that is operable in providing various functions for the vehicle 16 during flight, such as acting as a radar or a global positioning system. The main antenna 18 may be configured to send and/or receive signals and operable for target detection. The main antenna 18 may be cylindrical, or disc-shaped, and positioned along a longitudinal axis of the vehicle 16. As best shown in FIG. 1, during flight of the vehicle 16, a dense plasma sheath, or plasma field 20 is formed around the radome 12 of the vehicle 16. The plasma may be hot or cold. For example, the plasma may be cold if the vehicle 16 has a portion of travel through the ionosphere, the layer of the Earth's atmosphere that is ionized by solar and cosmic radiation. The plasma field 20 may be in a region surrounding the radome 12 of the vehicle 16 through which the main antenna 18 sends and/or receives signals. The plasma is generally dynamic and inhomogeneous such that the plasma field 20 inhibits the sending and/or receipt of signals by the main antenna 18.

The sensor system 10 and method of reducing plasma-induced communication inhibition may be implemented in the vehicle 16. The method includes detecting a density of plasma that affects operation of the main antenna 18 and re-orienting an electromagnetic field around the main antenna 18 in response to the density detected to reduce an effect of the plasma on the operation of the main antenna 18. The sensor system 10 and method includes at least one auxiliary antenna 22 that may be configured to perform multiple functions, including detecting the density of the plasma in the plasma field 20, re-directing or re-orienting the electromagnetic field that is generated by the auxiliary antenna 22, and providing data link communications for the vehicle 16.

Figure 5:
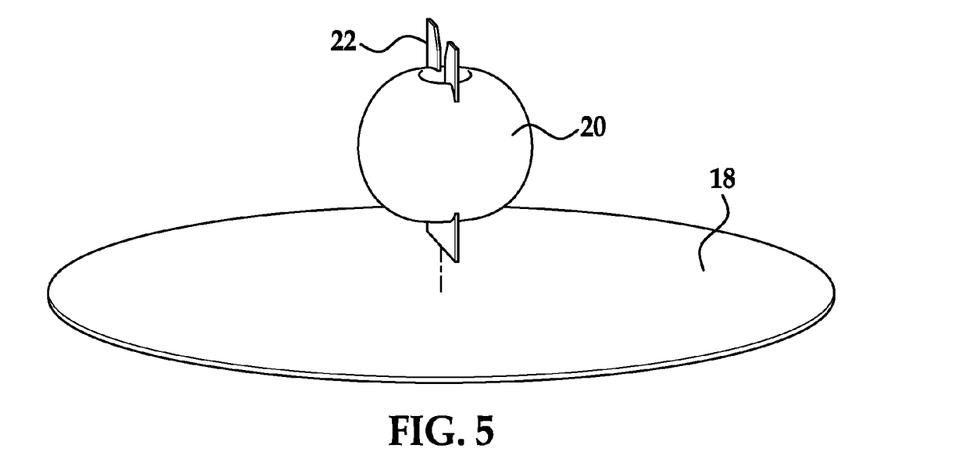
FIG. 5 is an oblique view of the auxiliary antenna of FIG. 3 in accordance with a second exemplary embodiment of the present invention.

One function of the auxiliary antenna 22 is operating as a dynamic sensor for measuring the amount or density of the plasma in the plasma field 20. As shown in FIGS. 3A-3D, the sensor system 10 may include a plurality of auxiliary antennas 22a, 22b that measure the plasma density by using scattering parameters or s-parameters of the auxiliary antennas 22a, 22b, and manipulate the plasma in response to the plasma density. Referring in addition to FIGS. 4 and 5, the auxiliary antennas 22a, 22b may have a dual mode capability, such that the auxiliary antennas 22a, 22b may be configured for plasma thickness sensing in a forward direction, as shown in FIG. 4, and in a sideways direction, as shown in FIG. 5. The s-parameters, the combination of the S-parameters between the forward and sideways capabilities of the auxiliary antennas 22a, 22b, and various ultra-wideband frequencies may be used as a sensor for plasma level measurements and the pattern orientation of the s-parameters may be adjusted or tilted by the auxiliary antennas 22 to accommodate for plasma dynamics. The plurality of auxiliary antennas 22a, 22b may be circumferentially spaced around the main antenna 18 such that the auxiliary antennas 22a, 22b may measure the return loss, or loss of power in a signal returned or reflected between the auxiliary antennas 22a, 22b, that is caused by the plasma field 20. The plurality of auxiliary antennas 22a, 22b may be circumferentially spaced and diametrically opposed to one another around the main antenna 18.

Another function of the auxiliary antenna 22 or auxiliary antennas 22a, 22b is sending signals regarding the density of the plasma 23 to re-orient an electromagnetic field of the sensor system 10. The auxiliary antenna 22 is configured to radiate or receive a time-varying electromagnetic field within the sensor system 10 that may be used to control or confine the plasma 23. At least one Poynting vector 23a, 23b, 23c is associated with the orientation of propagation of the electromagnetic waves through the plasma 23 of the plasma field 20, and in relation to the cross product of the electric and magnetic field of the auxiliary antenna 22. The Poynting vector 23a, 23b, 23c is also associated with the polarization of the auxiliary antenna 22. In a configuration having dual auxiliary antennas 22a, 22b, the plasma 23 may have a forward Poynting vector 23a and side Poynting vectors 23b, 23c. The orientation of the Poynting vectors 23a, 23b, 23c is dependent on the orientation of the plasma 23 in the plasma field. The plasma 23 may not have the same orientation at the tip region of the radome 12 and the side region of the radome 12, allowing the plasma 23 to move in the direction of any of the Poynting vectors 23a, 23b, 23c. As shown in FIG. 3B, the plasma 23 may move in the direction of the side Poynting vector 23b. As shown in FIGS. 3C and 3D, the plasma may move in the direction of another side Poynting vector 23c. The dual auxiliary antennas 22a, 22b are located at different positions within the radome 12 and the phase between the auxiliary antennas 22a, 22b may be adjusted to control the orientation of the radiation pattern between the auxiliary antennas 22a, 22b, and the Poynting vector 22a, 22b, 22c, or the electromagnetic field vector.

As best shown in FIG. 2, the sensor system 10 may further include an electrical conductor extending between a metallic charged tip 24 at the nose end 14 of the vehicle 16 and at least one charged plate 26 positioned at the main antenna 16. The metallic tip 24 and the metallic plate 26 may be operable to reduce the density of electrons in the plasma 23 by absorbing the electrons. Generally, the density of electrons has a directly proportional relationship to the plasma frequency, such that when the density of electrons is relatively high, the plasma frequency is also high. The density of the electrons in the plasma may also be proportional with the hypersonic speed of the vehicle 16. If the operational frequencies of the vehicle 16, such as a radio-frequency, are lower than the plasma frequency, the operational frequencies may not be able to penetrate through the plasma 23 to enable communications of the vehicle 16. The sensor system 10 is configured to reduce the density of the electrons and in turn, reduce the plasma frequency to a frequency that is lower than the operational frequencies of the vehicle 16. When the operational frequencies are higher than the plasma frequency, the operational frequencies may penetrate through the plasma frequency and allow for functions of the vehicle 16, such as communications.

To reduce the density of the electrons, the tip 24 and plate 26 within the radome 12 may absorb electrons and also positive ions of the plasma. Alternatively, a capacitor may be used. The electrical conductor extending between the tip 24 and the plate 26 may include any suitable conductor, such as wires. The sensor system 10 may include a plurality of charged plates 26 that are circumferentially spaced around the main antenna 16. The plurality of plates 26 may be positively charged to attract electrons of the plasma while the charged tip 24 may be negatively charged to attract positive ions of the plasma. The positive or negative potential on the plates allows the sensor system 10 to accommodate for the varying orientation of the plasma ions.

The plasma field 20 surrounding the radome 12 may be impacted by re-orienting the electromagnetic field. The auxiliary antenna 22 or the plurality of auxiliary antennas 22a, 22b may be configured to re-orient the electromagnetic field via a controller 28 that is operatively coupled to the auxiliary antennas 22, 22a, 22b. The controller 28 may be used to adjust a phase between the auxiliary antennas 22a and 22b re-orient the plasma, as shown in FIGS. 3B-D. The controller 28 is configured to receive information from the auxiliary antennas 22a, 22b regarding the plasma field 20.

Referring in addition to FIGS. 4 and 5, the auxiliary antennas 22a, 22b may have a dual mode capability, such that the auxiliary antennas 22a, 22b may be configured for plasma thickness sensing in a forward direction, as shown in FIG. 4, and in a sideways direction, as shown in FIG. 5. The return loss of the auxiliary antennas 22a, 22b is used to sense the thickness of plasma due to coupling effects. The forward mode of sensing has a return loss in the forward direction, and the sideways mode of the auxiliary antennas 22a, 22b has another return loss related to the side direction. The combination of readings and measurements in both the forward mode and the sideways mode provides information of the dynamics and/or shift of the plasma. Through the controller 28, the electric potential on the tip 24, which may initially be negative, and the electric potential at the plate 26, which may initially be positive, may be adjusted. The auxiliary antenna 22 may send a signal 30 to the controller 28 and in response to the signal 30, or feedback, the controller 28 may change the potential between the charged tip 24 and the charged plates 26 to re-orient the potential polarity between the charged tip 24 and plate 26. Reducing or removing the plasma in the area allows normal operation of the main antenna 18, such as acting as a sensor for target detection.

The information regarding the plasma may further be sent to electromagnets 32, 34, by way of the controller 28, to change the corresponding electromagnetic field and enabling the plasma to disperse. At least one electromagnet 32, 34 may be used to re-orient the electromagnetic field and impact the plasma field 20 surrounding the radome, with a particular focus on regions of the plasma field 20 that have a greater density of plasma. The sensor system 10 may include a plurality of electromagnets 32, 34 that are configured to repel or scatter the plasma to remove the plasma from the particular area of the main antenna 18 where signal conveyance is inhibited.

A positively charged electromagnet 30 and a negatively charged electromagnet 32 may be spaced apart within the radome 12 of the vehicle 16 to re-orient the electromagnetic field. The positively charged electromagnetic 30 may include a plurality of electromagnets 32 located at the perimeter of the main antenna 18. The plurality of electromagnets 32 may be circumferentially spaced around the main antenna 18 and diametrically opposed to one another along the perimeter of the main antenna 18. The negatively charged electromagnet 34 may be spaced apart from the plurality of positively charged electromagnets 32. The negatively charged electromagnet 34 may be positioned at a distally opposite end of the nose end 14 of the vehicle 16 from the positively charged electromagnets 32 and the main antenna 18. The negatively charged electromagnet 34 may be coupled to the metallic tip 24 of the vehicle 16.

The electromagnets may be used to create conditions within the sensor system 10 that are similar to the magnetic field of planet Earth. Generally, a greater amount of interference and penetration of cosmic rays and charged particles exists at the North Pole and South Pole. The magnetic field is weak along the orientation between the North Pole and the South Pole and charged particles may easily penetrate through or come into the atmosphere when aligned with the magnetic field. Charged particles have more difficulty penetrating through equator regions because the equator regions are oriented perpendicularly with respect to the orientation of the magnetic field. In the present application, the magnetic field orientation is dynamically re-oriented by changing the phase between windings of the electromagnets 32, 34, based on the feedback on plasma dynamics, or the density of the plasma that is sensed from the auxiliary antennas 22a, 22b.

The spaced apart electromagnets 32, 34 may have a fixed charge and an opposite polarity. At least one of the electromagnets 32, 34 may be a two-phase electromagnet such that, in response to the signal 26 sent by the auxiliary antenna 22, the controller 24 may be configured to change the orientation, or phase of one of the electromagnets 32, 34 relative to the other. The phase between the windings of the electromagnets 32, 34 may be used to change the orientation of the magnetic field, through feedback from the controller 24 and the auxiliary antennas 22 that measure the dynamics and fluctuations of plasma. The orientation of the magnetic field of the electromagnets 32, 34 may be changed to maximize the interaction of the electromagnetic field with the regions of the plasma field 20 that have denser plasma.

Referring now to FIGS. 4 and 5, another function of the at least one auxiliary antenna 22 includes providing data link communication, such as global positioning system communications. The auxiliary antenna 22 may be configured to have a dual capability in that the auxiliary antenna 22 acts as an antenna structure that sends and receives signals through the plasma field 20 in a forward direction at vertical polarization, as shown in FIG. 4, and towards a side direction at vertical polarization, as shown in FIG. 5. The auxiliary antenna 22 allows communication in different polarizations or orientations of the plasma field 20. Penetration through the plasma may occurs at a pre-determined polarization state of a radio-frequency signal and the sensor system 10 is advantageous in that it allows more degrees of freedom for penetration by the radio-frequency signal through the plasma.

The sensor system 10 may include a plurality of auxiliary antennas 22 that have a variable phase between one another for manipulating the plasma dynamically as previously described. The plurality of auxiliary antennas 22 may be operable for data link communication in a switchable manner such that if the density of the plasma inhibits receipt or sending of signals by one of the plurality of auxiliary antennas, another one of the plurality of auxiliary antennas 22 may be used for data link communication. The auxiliary antennas 22 may be operable for detecting the density of the plasma as previously described. The radiation pattern between the auxiliary antennas may be adjusted by introducing an appropriate phase shift of the auxiliary antennas. The patterns may be adjusted to allow for the plasma to be penetrated or for the switching of the auxiliary antennas 22 to enable for communication functions of the vehicle 16.

The auxiliary antenna 22 may have any suitable structure for a particular application. The auxiliary antenna 22 may have an ultra-wideband antenna structure that enables the transmission of ultra-wideband signals with varying polarization sub-bands. As shown in FIG. 4, the auxiliary antenna 22 may be configured as a forward-radiating, or Vivaldi-type antenna. The auxiliary antenna 22 may have a forward radiation pattern in a direction that is generally perpendicular to the main antenna 18 and parallel with the auxiliary antenna 22. As shown in FIG. 5, the auxiliary antenna 22 may have an omni-directional radiation pattern that is in a direction that is parallel with the main antenna 18 and perpendicular to the auxiliary antenna 22. The structure of the auxiliary antenna 22 is not limited to the aforementioned embodiments.

The sensor system and method as described herein has advantages over currently used systems and methods, such as providing fixed windows through plasma or providing solutions that only address the inhibition of communication without addressing the inhibition of target detection. The system and method accommodates for the inhomogeneity and dynamicity of plasma and uses a compact solution for multiple functions. The auxiliary antennas are used to clean the plasma around the radome to allow the main antenna to be operable for target detection. Additionally, the auxiliary antennas may be used for switchable data link communication and plasma sensing. Another advantage is that the auxiliary antennas 22 may be used in a form of adaptive space or polarization diversity for their use as "data link" or other applications in relationship to the plasma dynamics. For example, if the data link signal is weak in one of the auxiliary antennas, then, another one of the data link antennas may accommodate for the weakness by taking over the function. The accommodation by the other antenna is dependent on measured feedback from the s parameter measurements. In a similar approach, the auxiliary antennas 22 may use an adaptive polarization scheme to enhance data link communications. The polarization orientation of the system and method may be used to both manipulate the plasma reduction and improve data link communications for the radome.

Still another advantage is that the configuration of the auxiliary antennas allows the auxiliary antennas to exist in the same dome area as the main antenna without interfering with the main antenna. The system also makes use of existing components from the dome region, such as the metallic tip.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:
1. A sensor system comprising:
   a main antenna configured to send and/or receive radio-frequency signals;
   a plurality of auxiliary antennas configured to detect density of a surrounding plasma field that inhibits sending and/or receipt of the radio-frequency signals by the main antenna, wherein the auxiliary antennas are configured to generate an electromagnetic field and are operable for data link communication; and a controller operatively coupled to the at least one auxiliary antenna;

wherein the controller receives information from the at least one auxiliary antenna regarding the density of the plasma field; and wherein the controller is configured to adjust a phase between the auxiliary antennas, thereby reducing at least in part inhibition by the plasma field of the sending and/or receipt of signals of the main antenna.

2. The system of claim 1, wherein the plurality of auxiliary antennas are switchable with each other in response to density of the plasma field that inhibits the data link communication of one of the plurality of auxiliary antennas.

3. The system of claim 1, further comprising at least one electromagnet for re-orienting the electromagnetic field.

4. The system of claim 3, wherein the at least one electromagnet includes a positively charged electromagnet and a negatively charged electromagnet that are spaced apart, and one of the positively charged electromagnet and the negatively charged electromagnet is located distally opposite the main antenna.

5. The system of claim 4, further comprising a positively or negatively charged two-phase electromagnet that is operable to change phase relative to an oppositely charged electromagnet.

6. The system of claim 3, wherein the at least one electromagnet includes a plurality of electromagnets that are circumferentially spaced around the main antenna.

7. The system of claim 1, wherein the at least one auxiliary antenna includes a plurality of auxiliary antennas that are circumferentially spaced around the main antenna.

8. The system of claim 7, wherein the plurality of auxiliary antennas are diametrically opposed to one another.

9. The system of claim 1, wherein the system is contained in a radome of a hypersonic vehicle.

10. The system of claim 9, wherein the radome includes a metallic tip that is negatively or positively charged, and a plurality of charged plates having an opposite charge from the metallic tip that are circumferentially spaced around the main antenna, wherein the metallic tip is located distally opposite the plurality of charged plates.

11. The system of claim 10, further comprising an electromagnet coupled to the metallic tip for re-orienting the electromagnetic field.

12. The system of claim 1, wherein the at least one auxiliary antenna has an ultra-wideband antenna structure.

13. The system of claim 1, wherein the at least one auxiliary antenna has an omni-directional radiation pattern or a forward radiation pattern.

14. A method of reducing plasma-induced communication inhibition using the sensor system according to claim 1, the method comprising:

detecting a density of plasma that affects operation of the main antenna; and re-orienting the electromagnetic field around the main antenna in response to the density detected to reduce effect of the plasma on the main antenna.

15. The method of claim 14, further comprising using the plurality of auxiliary antenna to send information regarding the density of the plasma to the controller and re-orienting the electromagnetic field using the controller.

16. The method of claim 14, further comprising switching between a first and second auxiliary antenna for data link communication in response to the density detected in a respective region of the first and second auxiliary antenna.

17. The method of claim 15, further comprising using the at least one auxiliary antenna to detect the density of the plasma in a forward direction and a sideways direction.

18. A sensor system comprising:

a main antenna;

a plurality of auxiliary antennas that are circumferentially spaced around the main antenna and are diametrically opposed to one another; and a controller operatively coupled to the at least one auxiliary antenna;

wherein the controller receives information from the at least one auxiliary antenna regarding a plasma field that inhibits sending and/or receipt of signals by the main antenna; and wherein the controller configures an electromagnetic field set up by the at least one auxiliary antenna to reduce density of the plasma field, thereby reducing at least in part inhibition by the plasma field of the sending and/or receipt of signals of the main antenna, wherein the at least one auxiliary antenna includes a plurality of auxiliary antennas that are circumferentially spaced around the main antenna.

19. A sensor system contained in a radome of a hypersonic vehicle that includes a negatively or positively charged metallic tip, the sensor system comprising:

a main antenna;

at least one auxiliary antenna;

a controller operatively coupled to the at least one auxiliary antenna; and a plurality of charged plates having an opposite charge from the metallic tip that are circumferentially spaced around the main antenna, wherein the metallic tip is located distally opposite the plurality of charged plates, wherein the controller receives information from the at least one auxiliary antenna regarding a plasma field that inhibits sending and/or receipt of signals by the main antenna, and wherein the controller configures an electromagnetic field set up by the at least one auxiliary antenna to reduce density of the plasma field, thereby reducing at least in part inhibition by the plasma field of the sending and/or receipt of signals of the main antenna.

* * * * *